United States Patent [19]

Bouillon et al.

[11] 4,072,742
[45] Feb. 7, 1978

[54] ALUMINUM DERIVATIVES OF 2-PYRIDYL THIOL N-OXIDE, ROCESS FOR PREPARING THE SAME AND ANTIPERSPIRANT-DEODORANT COMPOSITION CONTAINING THE SAME

[75] Inventors: Claude Bouillon, Eaubonne; Georges Rosenbaum, Asnieres, both of France

[73] Assignee: L'Oreal, Paris, France

[21] Appl. No.: 635,441

[22] Filed: Nov. 26, 1975

Related U.S. Application Data

[62] Division of Ser. No. 294,072, Oct. 2, 1972, Pat. No. 3,953,450.

[30] Foreign Application Priority Data

May 12, 1972 Luxembourg .............. 65350

[51] Int. Cl.[2] .................. A61K 31/555; A61K 7/38; C07D 213/89
[52] U.S. Cl. ......................... 424/47; 424/68; 424/DIG. 5; 260/270 K
[58] Field of Search ............... 424/68, 47, DIG. 5; 260/270 K

[56] References Cited

U.S. PATENT DOCUMENTS 3,347,863 10/1967 Ottman .................. 260/270 K
3,953,450 4/1976 Bouillon ................ 260/270 K

*Primary Examiner*—Donald G. Daus
*Assistant Examiner*—Mark L. Berch
*Attorney, Agent, or Firm*—Cushman, Darby & Cushman

[57] ABSTRACT

An antiperspirant-deodorant composition containing in a cosmetic carrier an active compound of the formula

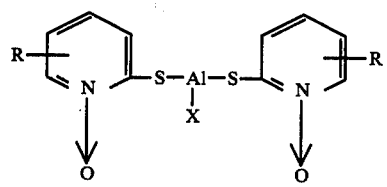

wherein X is chlorine, bromine and $R_1SO_3$ wherein $R_1$ is alkyl of 1-4 carbon atoms, phenyl, chlorophenyl, hydroxyphenyl and 2-oxo 10-bornanyl and R is hydrogen, chlorine, methyl or methoxy.

17 Claims, No Drawings

ALUMINUM DERIVATIVES OF 2-PYRIDYL THIOL N-OXIDE, PROCESS FOR PREPARING THE SAME AND ANTIPERSPIRANT-DEODORANT COMPOSITION CONTAINING THE SAME

This is a division of application Ser. No. 294,072, filed Oct. 2, 1972, now U.S. Pat. No. 3,953,450.

The present invention relates to a deodorant-antiperspirant cosmetic composition, to certain compounds usefully employed in these compositions and to a process for preparing these compounds.

It is well known that perspiration which results from the secretion of sudoriferous glands causes, on the one hand, moistness of the skin and, on the other, the appearance of body odors due to a decomposition of the perspiration by microorganisms.

To combat moistness of the skin it has heretofore been proposed to reduce perspiration by the application to the skin of conventional antiperspirant compound-containing compositions. These active compounds include, for instance, aluminum salts such as aluminum chlorhydroxide complex, known under the tradename CHLORHYDROL, sodium aluminum chlorhydroxy lactate complex, known under the tradename CHLORACEL, aluminum phenylsulfonate, aluminum chlorhydroxy allantoinate, aluminum dihydroxy allantoinate, aluminum isopropylate, and various other organic aluminum compounds, such as, for example, the complex combination of aluminum chlorhydroxide with propylene glycol known under the tradename REHYDROL.

While compositions including these conventionally known antiperspirant compounds may reduce perspiration, they do not at the same time effectively eliminate body odor which results from the decomposition of perspiration by microorganisms. Accordingly, in such compositions it was found necessary, in order to combat effectively the formation of body odor, to add a separate deodorant compound or agent which most often was an active agent against microorganisms. Thus, there resulted a composition containing an antiperspirant component or agent and an antimicrobe compound or agent, the latter generally being hexachlorophene.

However, such compositions, which are now widely used, still have certain drawbacks. For instance, it has been found that, in certain cases, the antiperspirant component or agent which can contain certain impurities as trace materials, actually inactivates to a significant degree, the antimicrobial action of the deodorant component or agent, thereby inhibiting to a significant degree the fulfilment of the double duty of the composition, i.e. its role as a perspiration inhibitor and as a deodorizer.

Further, it has also been found that the joint use of two active components which quite often are of very different nature and exhibit quite different physicochemical characteristics, poses very delicate and difficult problems on the formulation level. As will be appreciated, it is important, first of all, that there be no incompatibility, i.e. no interaction, between the two active components and secondly that there be no incompatability between either or both of these two components and the other components of the ultimate formulation.

Thus, it can easily be seen that the preparation of an acceptable formulation using two separate components, one for its antiperspirant activity, the other for its deodorizing effect, can present problems that are difficult, at best, for the formulator to overcome, especially if these active components exhibit substantially differing solubility characteristics for a given solvent. Ideally, then it would be desirable to use but a single component exhibiting multiple activity, i.e. one which would exhibit both acceptable perspiration inhibiting characteristics and deodorizing activity. Until now the art has not provided such a component. However, the applicants have found in a completely surprising way that certain aluminum compounds exhibit both effective perspiration inhibiting activity and effective deodorizing characteristics and the use of these aluminum compounds thus solves the problem of deodorant-antiperspirant compositions in the sense that, according to the invention, it is no longer necessary to add a separate antimicrobe or deodorant component to a composition containing a conventional antiperspirant aluminum compound to prevent not only the formation of body odors, but simultaneously to inhibit perspiration.

The compositions according to the present invention which bring about an undeniable technical advance, have been proven to exhibit both perspiration inhibiting activity at least equal and in many cases superior to conventionally known antiperspirant compositions and at the same time a powerful antimicrobe activity, while employing but one component to achieve both these desiderata.

Thus, one object of the present invention is to provide a deodorant-antiperspirant composition comprising in a suitable cosmetic vehicle as an active component a compound of the formula

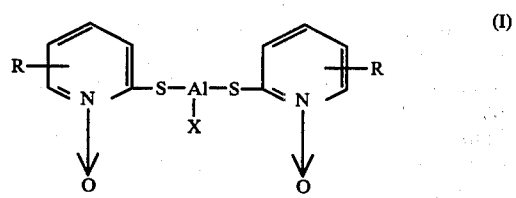

(I)

wherein X is selected from the group consisting of chlorine, bromine and $R_1SO_3$ wherein $R_1$ is selected from the group consisting of alkyl having from 1 to 4 carbon atoms, phenyl, p-chloro-phenyl, p-hydroxyphenyl and a 2-oxo 10-bornanyl, and each R independently represents a member selected from the group consisting of hydrogen, chlorine, methyl and methoxy.

Representative compounds of formula (I) that can be used in the composition of the present invention include bis-(2-N-oxypyridyl thio) aluminum chloride,
bis-(2-N-oxypyridyl thio) aluminum bromide,
bis-(2-N-oxypyridyl thio) aluminum camphosulfate,
bis-(2-N-oxypyridyl thio) aluminum p-toluene-sulfonate,
bis-(2-N-oxypyridyl thio) aluminum p-hydroxy-benzenesulfonate,
bis-(2-N-oxypyridyl thio) aluminum methanesulfonate,
bis-(4-chloro 2-N-oxypyridyl thio) aluminum chloride,
bis-(6-chloro 2-N-oxypyridyl thio) aluminum chloride,
bis-(4-methoxy 2-N-oxypyridyl thio) aluminum p-chlorobenzenesulfonate,
bis-(6-methoxy 2-N-oxypyridyl thio) aluminum bromide,
bis-(5-chloro 2-N-oxypyridyl thio) aluminum camphosulfonate and bis-(6-methyl 2-N-oxypyridyl thio) aluminum chloride.

The cosmetic composition according to the present invention can contain from 0.01 to 5 weight percent and preferably from 0.05 to 2%, of the active compound of formula (I) above, and can be provided in various forms, such as in the form of a lotion, a cream, a milk, a stick, a powder or in the form of an aerosol spray.

When the compositions according to the invention are in the form of a lotion for topical application to the skin or scalp, the concentration of active component is preferably between 0.01 and 0.1 weight percent.

These lotions comprise a solution of said active component in a solvent selected from the group consisting of water and an aqueous solution of a lower alkanol, such as ethanol or isopropanol, said aqueous solution of the lower alkanol generally containing from 30 to 90% by weight of said lower alkanol.

If desired, these lotions can also contain a conventional film forming cosmetic resin and thus provide a hair-setting lotion. Generally, the resin is one which has a molecular weight ranging from about 10,000 to 3,000,000 and is present in amounts of about 0.5 to 5% by weight.

Representative cosmetic resins that can be used include polyvinylpyrrolidone having a molecular weight between 10,000 and 70,000, polyvinylpyrrolidone/vinyl acetate copolymers (70–30%/30–70%), copolymers of vinyl acetate and an unsaturated carboxylic acid such as crotonic acid (molecular weight —20,000); copolymers resulting from polymerization of vinyl acetate (75–85%), crotonic acid (5–15%) and an acrylic or methacrylic ester (5–15%) or an alkyl vinyl ether (5–15%); copolymers resulting from the copolymerization of vinyl acetate (63–88%), crotonic acid (5–15%) and (a) (5–25%) of a vinyl ester of an acid with a long carbon chain having 10–22 carbon atoms or (b) of an allyl or methallyl ester of an acid with a long carbon chain having 10–22 carbon atoms; copolymers resulting from the copolymerization of 65–80% of an ester of an unsaturated alcohol having 2–12 carbon atoms and a saturated short carbon chain carboxylic acid having 2–5 carbon atoms, 7–12% of an unsaturated acid having 4–20 carbon atoms and 10–20% of at least an ester of a saturated alcohol having from 8–18 carbon atoms and an unsaturated acid having from 4–20 carbon atoms, and the copolymers resulting from the polymerization of at least an unsaturated ester and at least an unsaturated acid.

When the composition according to the present invention is in the form of a cream, the concentration of active component, in the cream base or carrier is preferably between 0.01 and 5 weight percent. The cream base or carrier is generally an oil-in-water emulsion comprising about 10–50 weight percent oil and 90–50 weight percent water.

Representative oils that can comprise the oil phase of the emulsion include:

(a) a hydrocarbon oil such as paraffin oil, purcellin oil, perhydrosqualene, and a solution of microcrystalline wax in an oil;
(b) animal or vegetable oil such as sweet almond oil, avocado oil, calophyllum oil, lanolin, castor oil, horse oil, pork oil and olive oil;
(c) mineral oil having an initial distillation point, at atmospheric pressure, of about 250° C and a final distillation point of about 410° C; and
(d) saturated ester such as isopropyl palmitate, alkyl myristates wherein the alkyl moiety is selected from isopropyl, butyl and cetyl, hexadecyl stearate, ethyl palmitate, triglyceride of octanoic and decanoic acid, and cetyl ricinoleate.

In the oil phase it is also possible to use silicone oils soluble in other oils, such as dimethylpolysiloxane, methyl-phenylpolysiloxane, and the silicon-glycol copolymer.

To promote the retention of oils, the oil phase can also contain waxes such as carnauba wax, candellila wax, beeswax, microcrystalline wax and ozokerite, the amount of wax employed generally ranging from about 0 to 20 percent by weight based on the weight of the oil employed in said oil phase.

Fatty alcohols such as stearyl alcohol, cetyl alcohol, 2-octyl 1-dodecanol, oxyethylenated fatty alcohols, propyleneglycol and the like, can also be used in making the creams according to the invention, said fatty alcohols usually being present in amounts of about 0.5 to 10 percent by weight of said composition.

When the compositions according to the invention are in the form of sticks, the concentration of active compound is preferably between 0.01 and 5 weight percent of said composition.

The antiperspirant-deodorant made in stick form in accordance with the present invention can be produced from a molten wax in which is incorporated the active compound of this invention. Generally, the active compound is incorporated into the stick as an emulsion of a solution thereof in water, in lower alkanol or in an aqueous solution of a lower alkanol, as defined above.

It has also been found advantageous, in the preparation of these antiperspirant-deodorant sticks to introduce into the wax component about 0.5 to 10 weight percent based on the weight of the wax, an oil or fatty alcohol, also as defined above.

The emulsifier employed to produce the antiperspirant-deodorant stick of this invention can be any conventional emulsifier generally used in cosmetic formulations of this type. In particular, it has been found that such emulsifiers as fatty amides, including diethanolamide and the like are usefully employed.

In the antiperspirant-deodorant sticks of the present invention, the aqueous, alcohol or dilute alcohol suspension or solution of the active component of the present invention represents about 0.5 to 20 percent by weight of the said stick.

When the composition according to the present invention is in powder form, the concentration of active component as defined above is preferably between 0.01 and 5 weight percent of the total weight of the composition.

These compositions in powder form contain, in addition to the said active component, a conventional powder base and a binder. The powder base can be any conventional essentially non-hygroscopic powder commonly used in cosmetic or pharmaceutical products. Illustrative of such materials are talc, starches such as rice starch or cornstarch, clay such as kaolin or bentonite, powdered stearates such as lithium stearate, zinc stearate and magnesium stearate; and mixtures of the same. Typical binders include, mineral oil, vegetable oil, lanolin, petroleum, fatty alcohols, iospropyl esters such as isopropyl myristate and isopropyl palmitate and the like.

Preferably, the cosmetic composition of the present invention is in the form of a sprayable aerosol which can be an alcohol-based spray or a dry or powder spray.

In this particular embodiment, the concentration of active component is generally between 0.01 and 5 weight percent of the total weight of the aerosol composition.

Alcohol-based spray in aerosol form contains, in addition to the active component of this invention, (a) an anhydrous alcohol selected from the group consisting of ethanol and isopropanol and (b) a liquified aerosol propellant under pressure such as a halogenated hydrocarbon including, for example, trichlorofluoromethane or dichlorodifluoromethane and their mixtures. Obviously, other conventional aerosol propellants, inert with respect to the active component of this invention can also be employed.

In the case of a dry or powder spray, the composition contains in addition to the active component of this invention and liquified propellant as defined above under pressure, a powder base and binder as defined above, the powder base being present in amounts of about 0.1 to 15 weight percent of the total aerosol composition and the binder, when present being included in amounts of about 0.05 to 5 percent by weight of said composition. Generally, the propellant is present in amounts of about 66 to 75 weight percent of the total aerosol composition, which is, of course, packaged under pressure.

It is understood that whatever particular form of the present invention is chosen, i.e. a cream, a stick, a lotion or an aerosol spray, any other component generally used in these types of cosmetic compositions which is inert with respect to the active component of this invention can be employed. For instance, it has been found advantageous to include in the composition of the present invention a preservative such as methyl parahydroxybenzoate or propyl parahydroxybenzoate, as well as a perfume.

It has been found that the active component of the present invention, in addition to exhibiting highly desirable antiperspirant characteristics, also exhibits excellent anti-microbial activity, particularly against the following microorganisms: Micrococcus aureus, Bacillus subtilis, Sarcina lutea, Escherichia coli, Aspergillus niger, Penicillium notatum, Mucor mucedo, Saccharomyses cerevisiae, Pityrosporum ovale, and Candida albicans.

Because of these particular properties, the composition of the present invention can effectively be used as cicatrizing, anti-dandruff compositions and for foot care and feminine hygiene. Additionally, the active compound of the present invention can also be used as a disinfectant and as a preserving or antiseptic agent.

The present invention also relates to a compound of the formula:

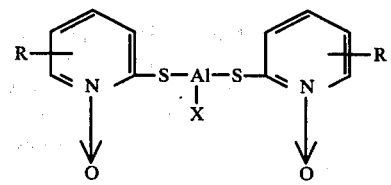

wherein X represents a member selected from the group consisting of isopropoxy, chlorine, bromine and $R_1SO_3$ wherein $R_1$ represents a member selected from the group consisting of alkyl having from 1 to 4 carbon atoms, phenyl, p-chlorophenyl, p-hydroxyphenyl and 2-oxo 10-bornanyl, and R represents a member selected from the group consisting of hydrogen, chlorine, methyl and methoxy.

Representative of compounds of the present invention are:

bis-(2-N-oxypyridyl thio) isopropoxy aluminum,
bis-(2-N-oxypyridyl thio) aluminum chloride,
bis-(2-N-oxypyridyl thio) aluminum bromide,
bis-(2-N-oxypyridyl thio) aluminum camphosulfonate,
bis-(2-N-oxypyridyl thio) aluminum p-toluenesulfonate,
bis-(2-N-oxypyridyl thio) aluminum p-hydroxybenzenesulfonate,
bis-(2-N-oxypyridyl thio) aluminum methanesulfonate,
bis-(4-chloro 2-N-oxypyridyl thio) aluminum chloride,
bis-(6-chloro 2-N-oxypyridyl thio) aluminum chloride,
bis-(4-methoxy 2-N-oxypyridyl thio) aluminum p-chlorobenzenesulfonate,
bis-(6-methoxy 2-N-oxypyridyl thio) aluminum bromide,
bis-(5-chloro 2-N-oxypyridyl thio) aluminum camphosulfonate, and
bis-(6-methyl 2-N-oxypyridyl thio) aluminum chloride.

The present invention is also related to a process for preparing these compounds, which process can be represented by the following scheme.

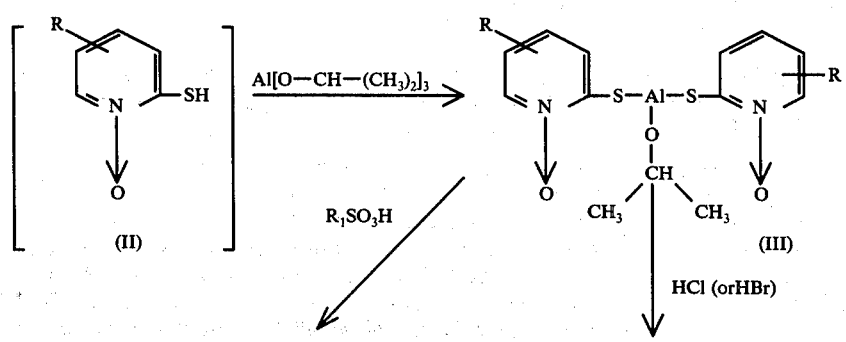

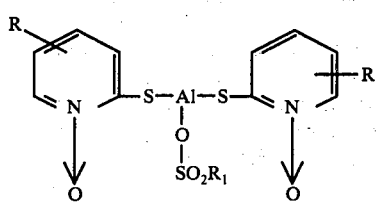

(Ib)

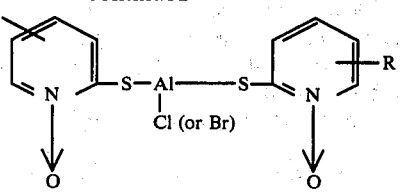

(Ia)

As can be seen from the reaction scheme represented above, the process comprises initially reacting aluminum isopropylate with an N-oxide of 2-pyridine thiol, (formula II) to produce a bis-(2-N oxypyridyl thio) isopropoxy aluminum (formula III) as an intermediate. Generally, the mole ratio of N-oxide of 2-pyridine thiol to aluminum isopropylate is 2:1 and the reaction is usually carried out in an anhydrous solvent such as an alcohol, and more particularly methyl, ethyl, isopropyl and tertio-butyl alcohol, an aromatic hydrocarbon such as benzene and toluene, or a chlorinated hydrocarbon such as chloroform and dichlorethane. Obviously other conventional anhydrous solvents, inert to the desired reaction, can also be used. The reaction can be carried out at ambient temperature or even at temperatures as high as about 50° C.

The resulting reaction product can, if desired, be isolated, and if isolated, the said reaction product is then suspended or dissolved in an anhydrous solvent, as defined above, prior to further reaction to produce the compound of the present invention. However, generally, the product of the reaction of aluminum isopropylate and an N-oxide of 2-pyridine thiol is not isolated and there is introduced into the reaction mixture containing this reaction product, represented by formula III, in an anhydrous solvent, an acid selected from the group consisting of hydrochloric acid, hydrobromic acid or sulfonic acid, said acid being employed in essentially stoichiometric proportions. When hydrochloric or hydrobromic acid is employed it can be introduced in the dry gaseous form or it can be introduced as a solution in an anhydrous solvent, as described above. When a sulfonic acid is employed it can be introduced in pure form or, again, as a solution in said anhydrous solvent. Generally, this step of the reaction is carried out at ambient temperature and at atmospheric pressure. In some cases the reaction is exothermic but it is not necessary to cool it.

There will now be given by way of illustration and without any limiting character several examples of preparation of the active compound of the present invention and some representative examples of the preparation of the deodorant-antiperspirant composition of the present invention employing these compounds.

EXAMPLES OF PREPARATION

EXAMPLE 1

Step 1 — Preparation and isolation of bis-(2-N-oxypyridyl thio isopropoxy aluminum (formula III wherein R = H).

Into a container provided with an agitator, there is added with stirring to a solution of 96.95 g of 2-pyridine thiol N-oxide in 196 ml of chloroform, a solution of 77.5 g of aluminum isopropylate in 392 ml of chloroform. Stirring is continued for 2 hours in the absence of light.

Then the chloroform and isopropanol, released during the reaction, are evaporated under reduced pressure from the reaction mixture, thus yielding 130.8 g (theory 129 g) of bis-(2-N-oxypyridyl thio) isopropoxy aluminum, a white product, whose sulfur determination corresponds approximately to the expected value.

Calculated %: S:18.94; Found %: S:18.56.

Step 2—Preparation of bis-(2-N-oxypyridyl thio) aluminum chloride.

130.8 g of bis-(2-N-oxypyridyl thio) isopropoxy aluminum prepared in accordance with the procedures of step 1, above, are suspended in 180 ml of chloroform. Then 71.6 ml of a solution of 5.33 N of dry gaseous hydrochloric acid in isopropanol are added. The resulting mixture is stirred for 1 hour and then concentrated to dryness under reduced pressure. 122.5 g of the desired product, a pink solid, is thus produced.

Calculated %: Cl:11.25; S:20.35; Found %: Cl:11.39 S:20.05.

EXAMPLE 2

Preparation of bis-(2-N-oxypyridyl thio) aluminum chloride without isolation of intermediate product of formula III A solution of 39.8 g of aluminum isopropylate in 105 ml of chloroform is added to a solution of 49.5 g of 2-pyridine thiol N-oxide in 100 ml of chloroform. The resulting mixture is stirred for 2 hours in the absence of light. Then 112 ml of a solution of 1.74 N of dry gaseous hydrochloric acid in isopropanol is added and stirred for 1 hour. After evaporation to dryness under reduced pressure, 61.5 g of the above product, pinkish white solid, are produced.

Calculated %: Cl:11.25; S:20.35; Found %: Cl:10.96; S:20.11.

EXAMPLE 3

Example 2 is repeated except that the dry gaseous hydrochloric acid is replaced by dry gaseous hydrobromic acid.

EXAMPLE 4

Example 2 is repeated except that 2-pyridine thiol N-oxide is replaced by the chloro derivative thereof.

EXAMPLE 5

Example 2 is repeated except that 2-pyridine thiol N-oxide is replaced by the methyl derivative thereof.

EXAMPLE 6

Preparation of bis-(2-N-oxypyridyl thio) aluminum methanesulfonate

A solution of 10.2 g of aluminum isopropylate in 100 ml of chloroform is added to a solution of 12.7 g of 2-pyridine thiol N-oxide in 100 ml of chloroform. The resulting mixture obtained is stirred for 2 hours, and then treated with a solution of 4.8 g of methanesulfonic acid in 50 ml of chloroform. Stirring is continued for 1 hour and then the solvent is evaporated under reduced pressure, yielding 18.7 g of a solid whitish product.

Calculated %: S:25.65; Found %: S:25.09.

EXAMPLE 7

Example 6 is repeated except that 2-pyridine thiol N-oxide is replaced by the methoxy derivative thereof.

EXAMPLE 8

Example 6 is repeated except that 2-pyridine thiol N-oxide is replaced by the methyl derivative thereof.

EXAMPLE 9

Preparation of bis-(2-N-oxypyridyl thio) aluminum camphosulfonate.

A solution of 17.5 g of 2-pyridine thiol N-oxide in 35 ml of chloroform is added to a solution of 14 g of aluminum isopropylate in 50 ml of chloroform. The resulting mixture is stirred for 2½ hours in the absence of light. Then a solution of 15.7 g of 10-camphosulfonic acid in 220 ml of ethyl acetate is added and the resulting mixture if stirred for 1 hour. The solvents are then evaporated under reduced pressure, yielding 35.6 g of bis-(2-N-oxypyridyl thio) aluminum camphosulfonate, a slightly grayish solid product.

Calculated %: Al:5.29; Found %: Al:5.27.

EXAMPLE 10

Example 9 is repeated except that 10-camphosulfonic acid is replaced by phenyl sulfonic acid.

EXAMPLE 11

Example 9 is repeated except that 10-camphosulfonic acid is replaced by p-chlorophenylsulfonic acid.

EXAMPLE 12

Example 9 is repeated except that 10-camphosulfonic acid is replaced by p-hydroxyphenylsulfonic acid.

EXAMPLES OF COMPOSITIONS

EXAMPLE 13

There is prepared, in accordance with the present invention, a deodorant lotion exhibiting anti-dandruff activity, for the scalp, by mixing the following components:

| | |
|---|---|
| Bis-(2-N-oxypyridyl thio) aluminum chloride | 0.1 g |
| Camphor | 0.1 g |
| Menthol | 0.05 g |
| Ethanol | 50 g |
| Water, q.s.p. | 100 g |

This lotion, applied weekly to the hair, effectively reduces dandruff and prevents the formation of any body odor originating from the scalp.

EXAMPLE 14

There is prepared in accordance with the present invention an antiperspirant-deodorant setting lotion by mixing the following components:

| | |
|---|---|
| Bis-(2-N-oxypyridyl thio) aluminum chloride | 0.05 g |
| Polyvinylpyrrolidone (molecular weight 40,000 | 2 g |
| Lanolin oxyethylenated with 16 moles of ethylene oxide | 0.3 g |
| Mink oil | 0.05 g |
| Nonylphenol oxyethylenated with 5 moles ethylene oxide | 0.5 g |
| Ethanol | 40 g |
| Water, q.s.p. | 100 g |

EXAMPLE 15

There is prepared, in accordance with the present invention, an antiperspirant-deodorant cream by mixing the following components:

| | |
|---|---|
| Cetyl-stearyl alcohol oxyethylenated with 15 moles of ethylene oxide | 10 g |
| Cetyl alcohol | 2 g |
| Spermaceti | 2 g |
| Vaseline oil | 5 g |
| Sweet almond oil | 1 g |
| Rosemary oil | 0.2 g |
| Lavender oil | 0.3 g |
| Geranium oil | 0.1 g |
| Bis-(2-N-oxypyridyl thio) aluminum methanesulfonate | 2 g |
| Water, q.s.p. | 100 g |

EXAMPLE 16

There is prepared in accordance with the present invention an antiperspirant-deodorant cream for foot care by mixing the following components:

| | |
|---|---|
| Self-emulsifying glycerol stearate | 6 g |
| Stearic acid | 2 g |
| Castor oil | 2 g |
| Vaseline oil | 5 g |
| Isopropyl myristate | 3 g |
| Allantoin | 0.3 g |
| Camphor | 0.3 g |
| Menthol | 0.2 g |
| Bis-(2-N-oxypyridyl thio) aluminum camphosulfonate | 2.7 g |
| Triethanolamine | 0.1 g |
| Water, q.s.p. | 100 g |

EXAMPLE 17

There is prepared, in accordance with the present invention, an antiperspirant-deodorant milk by mixing the following components:

| | |
|---|---|
| Sorbitan sesquioleate | 2 g |
| Glycerol stearate | 5 g |
| Lanolin | 1 g |
| Lanolin oxyethylenated with 16 moles ethylene oxide | 1 g |
| Hexamethyltetracosane | 5 g |
| "carbopol", a carboxyvinyl polymer sold by the B.F. Goodrich Chemical Company (Merck Index, 1968 ed., p.210) | 0.5 g |
| Triethanolamine, q.s.p. | pH 7 |
| Ethanol | 10 g |
| Bis-(2-N-oxypyridyl thio) aluminum chloride | 1.2 g |
| Perfume | 0.5 g |
| Water, q.s.p. | 100 g |

EXAMPLE 18

There is prepared, in accordance with the present invention, an emulsion for an antiperspirant-deodorant, in roll-on form by mixing the following components:

| | |
|---|---|
| Lauryl alcohol oxyethylenated with 2 to 3 moles of ethylene oxide | 0.5 g |
| Vaseline oil | 2.5 g |
| Lanolin | 1 g |

-continued

| | |
|---|---|
| Stearyl and cetyl alcohols (50/50 mixture) | 1.5 g |
| Wheat starch | 2 g |
| 2-chloro bis-5,5-(ethoxycarbonyl) 1,2,3-dioxalumane | 4 g |
| Bis-(2-N-oxypyridyl) aluminum bromide | 1.5 g |
| Water, q.s.p. | 100 g |

EXAMPLE 19

There is prepared in accordance with the present invention, an antiperspirant-deodorant milk bath by mixing the following components:

| | |
|---|---|
| Magnesium lauryl sulfate | 20 g |
| Colloidal silica | 6 g |
| Fatty acid glycerides (C 14 to C 18) | 5 g |
| Bis-(4-chloro 2-N-oxypyridyl thio) aluminum chloride | 0.4 g |
| Microencapsulated perfume | 20 g |
| Whole powdered milk, q.s.p. | 100 g |

EXAMPLE 20

There is prepared, in accordance with the present invention, an antiperspirant-deodorant body foam by mixing the following components and packaging the same under pressure:

| | |
|---|---|
| Bis-(6-chloro 2-N-pxypyridyl thio) aluminum chloride | 0.05 g |
| Citronellyl senecioate | 1g |
| Miranol C₂M (sold by the Miranol Company), a product of the reaction of 1-β-hydroxy-S ethyl 2-undecyl 2-Δimidazoline with sodium chloroacetate | 2 g |
| Glycerin | 10 g |
| Fatty alcohols (C 16 to C 18) oxyethylenated with 15 moles of ethylene oxide | 0.5 g |
| Perfume | 0.5 g |
| Water | 75.95 g |
| Dichlorodifluoromethane | 10 g |

EXAMPLE 21

There is prepared in accordance with the present invention, an antiperspirant-deodorant body lotion for dry skin by mixing the following components:

| | |
|---|---|
| Bis-(2-N-oxypyridyl thio) aluminum chloride | 1 g |
| Keratin proteolysate | 10 g |
| d-1 norvaline | 0.5 g |
| Aqueous placental extract | 5 g |
| Sodium alginate | 0.5 g |
| Vaseline oil | 5 g |
| Lanolin | 1 g |
| Oleyl alcohol oxyethylenated with 8 moles ethylene oxide | 5 g |
| Water, q.s.p. | 100 g |

EXAMPLE 22

There is prepared in accordance with the present invention, an antiperspirant-deodorant spray for the scalp by mixing the following components and packaging the same under pressure:

| | |
|---|---|
| Bis-(2-N-oxypyridyl thio) aluminum chloride | 0.1 g |
| Hexylene glycol | 2 g |
| Ethanol | 12.4 g |
| Oil of marjoram | 0.5 g |
| Trichlorofluoromethane | 54 g |
| Dichlorodifluoromethane | 31 g |

EXAMPLE 23

There is prepared in accordance with the present invention an antiperspirant-deodorant spray by mixing the following components:

| | |
|---|---|
| Bis-(2-N-oxypyridyl thio) aluminum p-toluenesulfonate | 0.5 g |
| Partially methylated colloidal silica | 0.3 g |
| Diethyl sebacate | 6 g |
| Starch | 2 g |
| Lanolin oxyethylenated with 16 moles ethylene oxide | 0.5 g |
| Perfume | 0.7 g |
| Trichlorofluoromethane | 45 g |
| Dichlorodifluoromethane | 45 g |

EXAMPLE 24

There is prepared in accordance with the present invention, a dry antiperspirant-deodorant spray by mixing the following components and packaging the same under pressure:

| | |
|---|---|
| Bis-(2-N-oxypyridyl thio) aluminum p-hydroxybenzenesulfonate | 4.1 g |
| Aluminum basic hydrochloride | 3.4 g |
| Partially methylated colloidal silica | 0.2 g |
| Silicone fluid oil | 4.6 g |
| Perfume | 0.7 g |
| Trichlorofluoromethane | 34 g |
| Dichlorodifluoromethane | 53 g |

EXAMPLE 25

There is prepared in accordance with the present invention, a dry antiperspirant-deodorant spray to be used after the bath by mixing the following components and packaging the same under pressure:

| | |
|---|---|
| Fatty alcohol triglycerides (C 16 to C 18) | 5 g |
| Butyl stearate | 4 g |
| Avocado oil | 0.5 g |
| Lecithin | 0.45 g |
| Bis-(4-methoxy 2-N-oxypyridyl thio) aluminum p-chloro benzenesulfonate | 0.05 g |
| Trichlorofluoromethane | 54 g |
| Dichlorodifluoromethane | 36 g |

EXAMPLE 26

There is prepared, according to the invention, an antiperspirant-deodorant spray for delicate skin by mixing the following components and packaging the same under pressure:

| | |
|---|---|
| Diethyl para-aminobenzoate | 0.5 g |
| Azulene | 0.10 g |
| Bis-(2-N-oxypyridyl thio) aluminum chloride | 0.01 g |
| Wheat germ oil | 1 g |
| Ethylhexyl adipate | 10.3 g |
| Trichlorofluoromethane | 54 g |
| Dichlorodifluoromethane | 34 g |

EXAMPLE 27

There is prepared in accordance with the present invention, an antiperspirant-deodorant spray by mixing the following components and packaging the same under pressure:

| | |
|---|---|
| Panthenol | 0.5 g |

| | |
|---|---|
| Isopropyl myristate | 2 g |
| Bis-(2-N-oxypyridyl thio) aluminum chloride | 0.1 g |
| Perfume | 0.5 g |
| Isopropanol | 36.9 g |
| Trichlorofluoromethane | 36 g |
| Dichlorodifluoromethane | 24 g |

EXAMPLE 28

There is prepared in accordance with the present invention, an antiperspirant-deodorant powder spray for foot care by mixing the following components:

| | |
|---|---|
| Bis-(6-methoxy 2-N-oxypyridyl thio) aluminum bromide | 3.9 g |
| Titanium oxide | 5 g |
| Kaolin | 5 g |
| Aluminum basic hydrochloride | 3 g |
| Oil of lavender | 1 g |
| Talc (20 microns), q.s.p. | 100 g |

10 g of this composition are packaged in an aerosol container in the presence of 54 g of trichlorofluoromethane and 36 g of dichlorodifluoromethane.

EXAMPLE 29

There is prepared in accordance with the present invention, an antiperspirant-deodorant talc by mixing the following components:

| | |
|---|---|
| Magnesium stearate | 5 g |
| Zinc oxide | 5 g |
| Boric acid | 2 g |
| Undecylenic acid | 0.2 g |
| Bis-(6-methyl 2-N-oxypyridyl thio) aluminum chloride | 5 g |
| Talc, q.s.p. | 100 g |

EXAMPLE 30

There is prepared in accordance with the present invention, an antiperspirant-deodorant composition for impregnating fabrics for feminine hygiene by mixing the following components:

| | |
|---|---|
| Bis-(2-N-oxypyridyl thio)aluminum chloride | 0.1 g |
| Ethanol | 70 g |
| Perfume | 1 g |
| Water, q.s.p. | 100 g |

150 cm² of unwoven fabric are impregnated with 4 cc of the above solution.

EXAMPLE 31

There is prepared in accordance with the present invention, an antiperspirant-deodorant composition to impregnate fabrics for feminine hygiene by mixing the following components:

| | |
|---|---|
| Bis-(2-N-oxypyridyl thio) aluminum camphosulfonate | 0.35 g |
| Ethanol | 70 g |
| Perfume | 1 g |
| Water, q.s.p. | 100 g |

150 cm² of unwoven fabric are impregnated with 4 cc of this solution.

What is claimed is:

1. An antiperspirant-deodorant composition comprising in a cosmetic carrier as the active compound to inhibit perspiration and the formation of body odor, an effective amount of a compound having the formula

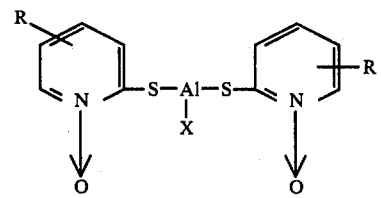

wherein X is selected from the group consisting of chlorine, bromine and $R_1SO_3$ wherein $R_1$ is selected from the group consisting of alkyl having from 1 to 4 carbon atoms, phenyl, p-chlorophenyl, p-hydroxyphenyl and 2-oxo 10-bornanyl, and R represents a member selected from the group consisting of chlorine, methyl and methoxy.

2. The composition of claim 1 wherein said active compound is selected from the group consisting of bis-(2-N-oxypyridyl thio) aluminum chloride,
bis-(2-N-oxypyridyl thio) aluminum bromide,
bis-(2-N-oxypyridyl thio) aluminum camphosulfonate,
bis-(2-N-oxypyridyl thio) aluminum p-toluenesulfonate,
bis-(2-N-oxypyridyl thio) aluminum p-hydroxybenzenesulfonate,
bis-(2-N-oxypyridyl thio) aluminum methanesulfonate,
bis-(4-chloro-2-N-oxypyridyl thio) aluminum chloride,
bis-(6-chloro-2-N-oxypyridyl thio) aluminum chloride,
bis-(4-methoxy-2-N-oxypyridyl thio) aluminum p-chlorobenzenesulfonate,
bis-(6-methoxy-2-N-oxypyridyl thio) aluminum bromide,
bis-(5-chloro-2-N-oxypyridyl thio) aluminum camphosulfonate and
bis-(6-methyl-2-N-oxypyridyl thio) aluminum chloride.

3. The composition of claim 1 wherein said active compound is present in an amount between 0.01 and 5% by weight of said composition.

4. The composition of claim 1 wherein said active compound is present in an amount of about 0.05 and 2% by weight of said composition.

5. The composition of claim 1 in the form of a lotion, cream, stick, powder or aerosol spray.

6. The composition of claim 1 in lotion form, wherein said active compound is present in an amount of about 0.01 and 0.1% by weight of said composition and wherein said cosmetic carrier is selected from the group consisting of water and an aqueous solution of a lower alkanol selected from the group consisting of ethanol and isopropanol.

7. The composition of claim 1 in aerosol spray form and packaged under pressure wherein said active compound is present in an amount of about 0.01 to 5% by weight of said composition and which also includes liquified propellant gas under pressure.

8. The composition of claim 1 in cream form, wherein said active compound is present in an amount of about 0.01 to 5% by weight of said composition and wherein said cosmetic carrier is a water-in-oil emulsion.

9. The composition of claim 8, wherein said water-in-oil emulsion comprises about 10–50 weight percent oil and 90–50 weight percent water.

10. The composition of claim 1 in stick form, wherein said active compound is present in an amount of about 0.01 to 5% by weight of said composition and is emulsified in said cosmetic carrier which is a mixture of a member selected from the group consisting of water, lower alkanol or a mixture thereof and wax.

11. The composition of claim 1 in powder form wherein said active compound is present in an amount of about 0.01 to 5% by weight of said composition and wherein said cosmetic carrier is talc.

12. The composition of claim 7 which also includes an anhydrous alcohol selected from the group consisting of ethanol and isopropanol.

13. The composition of claim 7 which also includes talc.

14. A compound of the formula

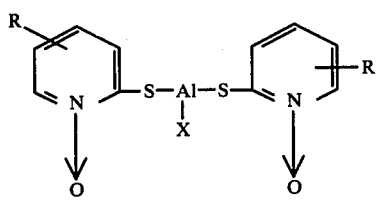

wherein X is $R_1SO_3$ wherein $R_1$ represents a member selected from the group consisting of alkyl having from 1 to 4 carbon atoms, phenyl, p-methylphenyl, p-chlorophenyl, p-hydroxyphenyl and 2-oxo 10-bornanyl radical and R represents a member selected from the group consisting of chlorine, methyl and methoxy.

15. The compound of claim 14 selected from the group consisting of bis-(2-N-oxypyridyl thio) aluminum camphosulfonate,
bis-(2-N-oxypyridyl thio) aluminum p-toluenesulfonate,
bis-(2-N-oxypyridyl thio) aluminum p-hydroxybenzenesulfonate,
bis-(2-N-oxypyridyl thio) aluminum methanesulfonate,
bis-(4-methoxy 2-N-oxypyridyl thio) aluminum p-chlorobenzenesulfonate and
bis-(5-chloro 2-N-oxypyridyl thio) aluminum camphosulfonate.

16. A process for preparing a compound of claim 14 comprising reacting in an anhydrous solvent selected from the group consisting of methanol, ethanol, isopropanol, tertio-butyl alcohol, benzene, toluene, chloroform and dichlorethane, a 2-pyridine thiol N-oxide of the formula

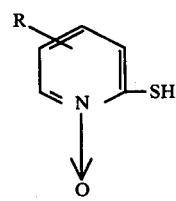

wherein R represents a member selected from the group consisting of hydrogen, chlorine, methyl and methoxy, with aluminum isopropylate and reacting the resulting reaction product with sulfonic acid having the formula $R_1SO_3H$ wherein $R_1$ represents a member selected from the group consisting of alkyl having 1-4 carbon atoms, phenyl, p-methylphenyl, p-chlorophenyl, p-hydroxyphenyl and 2-oxo 10-bornanyl.

17. The process of claim 16 wherein the molar ratio of said 2-pyridine thio N-oxide to aluminum isopropylate is 2:1.

* * * * *